United States Patent [19]

Sahota

[11] Patent Number: 4,581,017
[45] Date of Patent: Apr. 8, 1986

[54] CATHETER SYSTEMS
[76] Inventor: Harvinder Sahota, 3861 Wisteria, Seal Beach, Calif. 90740
[21] Appl. No.: 473,063
[22] Filed: Mar. 7, 1983
[51] Int. Cl.$^4$ ............................................. A61M 29/00
[52] U.S. Cl. ...................................... 604/101; 604/102
[58] Field of Search .......... 128/344; 604/96, 101–102, 604/281

[56] References Cited
U.S. PATENT DOCUMENTS

| | | | |
|---|---|---|---|
| 2,930,377 | 3/1960 | Cowley | 604/103 |
| 3,889,686 | 6/1975 | Duturbure | 604/102 |
| 4,040,413 | 8/1977 | Ohshiro | 604/101 |
| 4,233,983 | 11/1980 | Rocco | 604/102 |
| 4,329,993 | 5/1982 | Lieber et al. | 604/101 |
| 4,423,725 | 1/1984 | Baran et al. | 604/101 |

OTHER PUBLICATIONS

Bourassa Cardiovascular Catheters 6–1972 (4 pages).
A New Catheter System for Coronary Angioplasty, The American Journal of Cardiology, vol. 49, pp. 1216–1222, Apr. 1, 1982.

Primary Examiner—C. Fred Rosenbaum
Assistant Examiner—Gene B. Kartchner
Attorney, Agent, or Firm—Knobbe, Martens, Olson & Bear

[57] ABSTRACT

Catheter systems provide blood flow paths past a stenotic region of a blood vessel receiving treatment to restore acceptable blood flow. A catheter includes distal and proximal side orifices into a main lumen to provide a blood flow path through the catheter across the stenosis. A segmented or lobed balloon forms blood flow passages between the catheter and blood vessel wall to provide blood flow past the stenosis while the balloon is inflated. Superselective catheter systems provide means for inserting a catheter into coronary arteries remote from the aorta.

8 Claims, 23 Drawing Figures

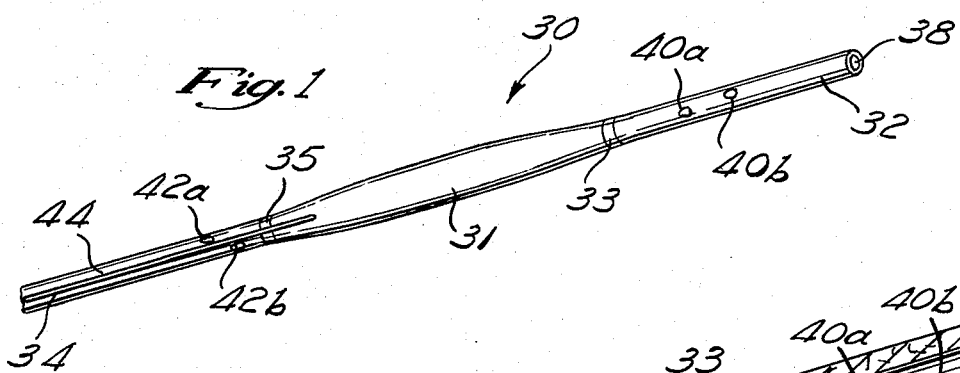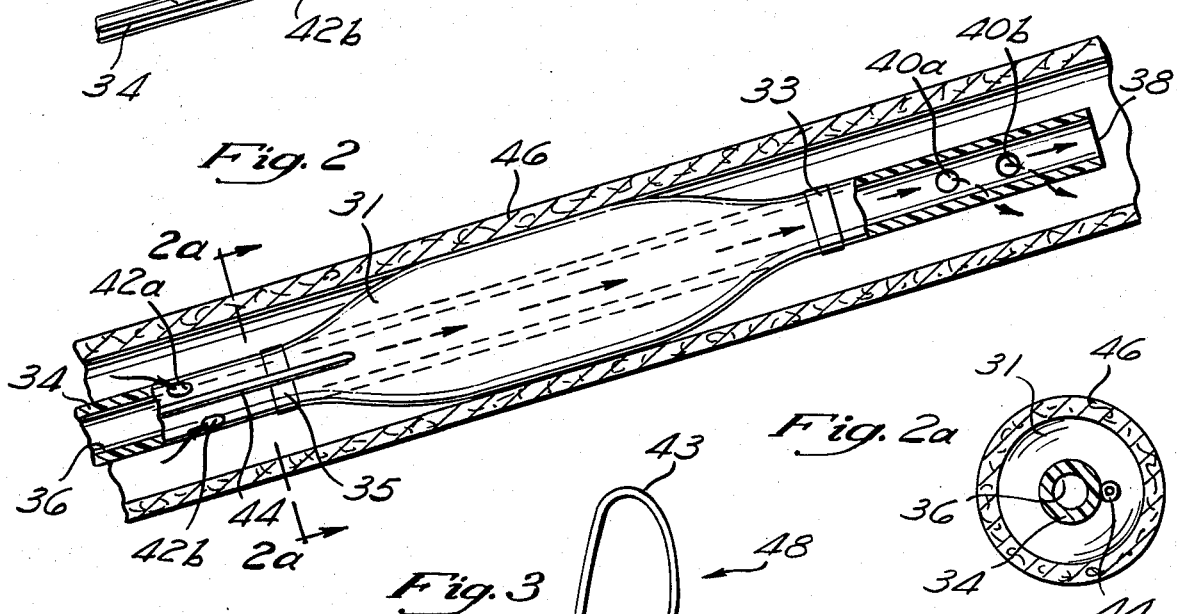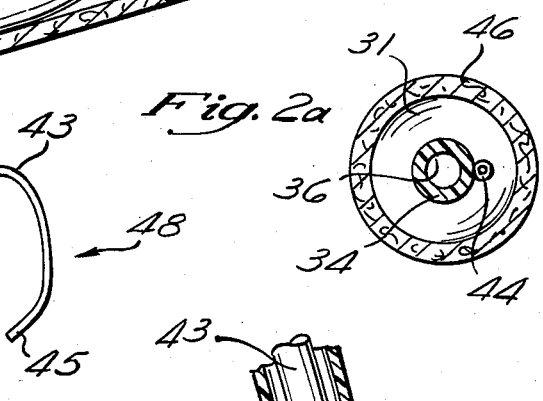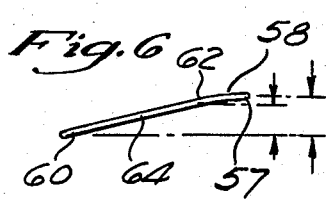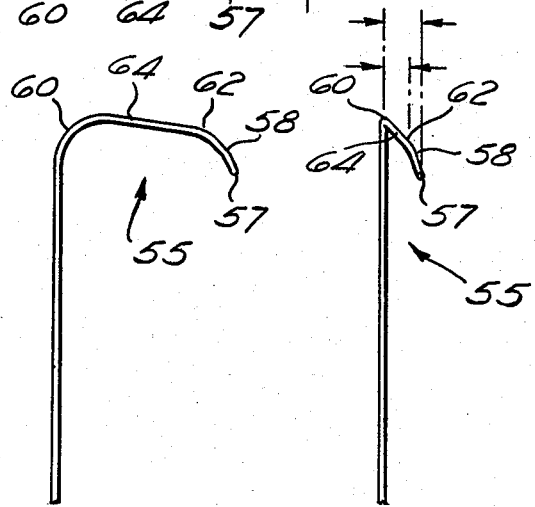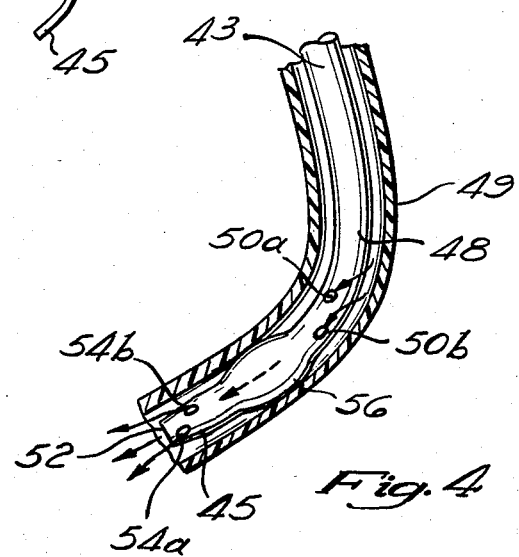

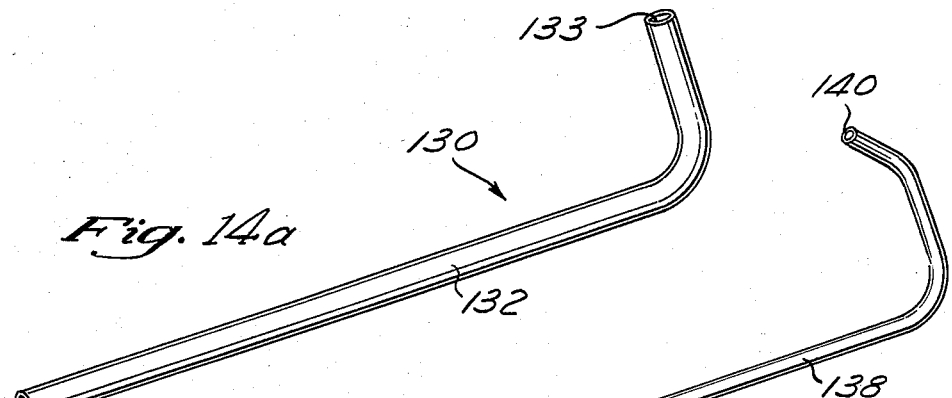
Fig. 14a
Fig. 14b
Fig. 14c
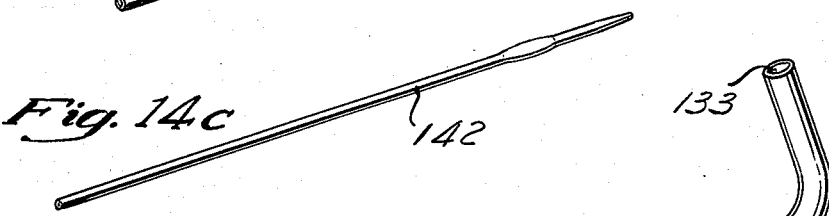
Fig. 15
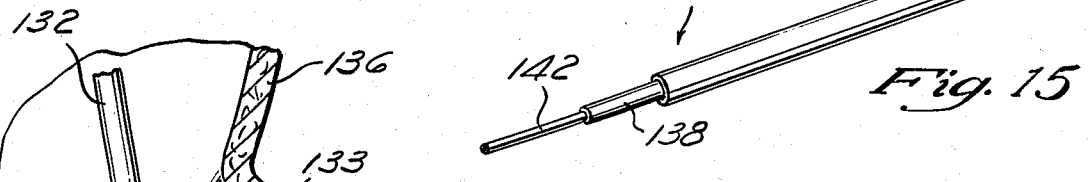
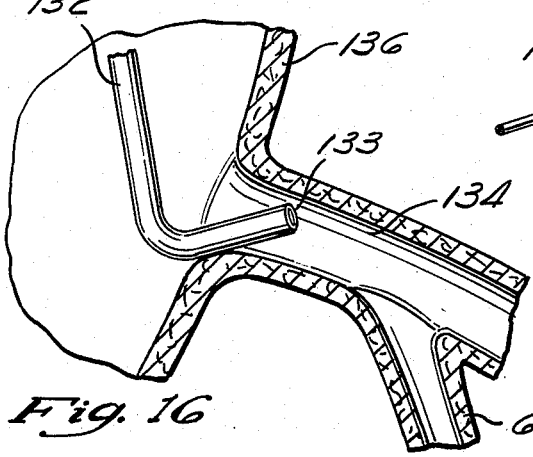
Fig. 16
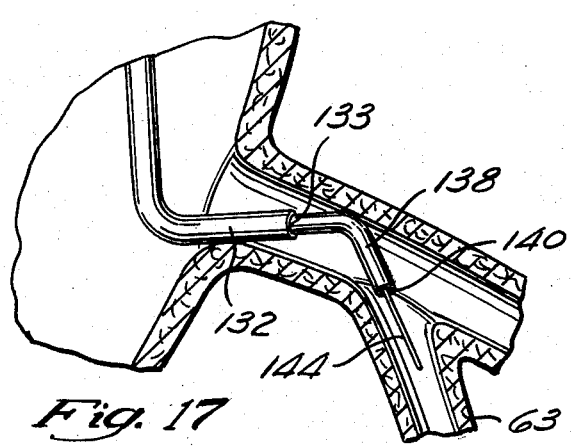
Fig. 17
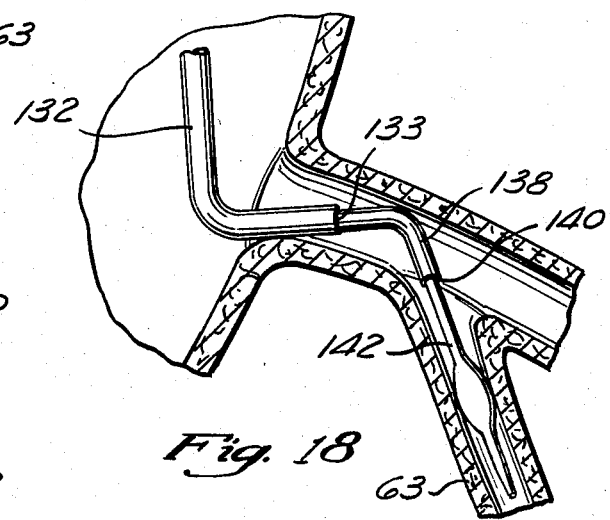
Fig. 18

CATHETER SYSTEMS

BACKGROUND OF THE INVENTION

This invention relates generally to catheters and particularly to coronary dilatation catheters for use in administering treatments to widen a constricted blood flow passage in, for example, a heart valve or a coronary artery.

A stenosis is a region of a blood vessel which has been narrowed to such a degree that blood flow is restricted. If the stenosis is sufficiently severe, treatment is required to restore adequate blood flow. Often such treatment requires surgery or angioplasty. Percutaneous transluminal coronary angioplasty is a procedure for treating a patient having a stenosis or constricted region in a coronary artery. In some patients it is possible to expand a stenosis so that the artery will permit an acceptable blood flow rate.

Coronary angioplasty comprises the insertion of a balloon catheter through the patient's left femoral artery and heart into the arterial stenosis and injecting a suitable fluid into the balloon to expand the stenosis radially outward, compressing the stenosis against the arterial wall. Therefore, angioplasty has become an alternative to coronary arterial bypass surgery for many patients. If the stenosis is comprised primarily of fatty deposits, rather than an appreciable amount of calcium, and if the stenosis is not too severe, it is often possible to compress the stenosis radially outward against the adjacent arterial wall to increase the cross sectional area of the artery so that the artery has an acceptable blood flow rate therethrough.

Ordinary balloon catheters have a balloon fastened around the exterior of a hollow catheter tube. A thin line fastened to the balloon and the exterior surface of the catheter provides means for connecting the balloon to a suitable fluid supply for inflating the balloon. The hollow catheter tube provides means for injecting fluids into the artery for diagnostic and therapeutic purposes.

Prior coronary dilatation catheters used in coronary angioplasty have the disadvantage of completely occluding blood flow while the balloon is expanded in the artery. Any complete occlusal of a coronary artery cannot be permitted for more than about ten seconds without incurring serious risk of damage to the portions of the heart which should receive blood from the occluded artery. Therefore, the balloon may be pressurized for only a few seconds before the balloon must be allowed to depressurize for permitting resumption of blood flow through the region of the stenosis.

The problem of occluding blood flow is particularly acute in patients having a left main coronary artery lesion. Ordinary catheters even without balloons may cause spasm by narrowing the left main coronary artery, which supplies blood to a large portion of the heart.

A cardiologist administering an angioplasty treatment ordinarily does not know exactly how much pressure to apply to the balloon to achieve satisfactory results. Excessive pressure in the balloon may dissect the artery, which may cause serious damage to the patient's heart. Therefore, the cardiologist positions the balloon in the artery, expands the balloon, allows the balloon to depressurize and removes the catheter from the artery to permit measurement of the blood flow rate past the stenosis. If the blood flow rate is not acceptable, then the cardiologist repeats the angioplasty treatment until the blood flow rate is acceptable or until the cardiologist determines that angioplasty will be unable to restore the blood flow rate to an acceptable value.

It is possible that the mere presence of an ordinary balloon catheter into the stenosis for more than ten seconds will seriously occlude blood flow and cause a risk of heart damage. It is also possible for a patient's artery to experience a complete occlusal or blockage after the balloon catheter is withdrawn from the artery. Rapid restoration of blood flow is necessary to prevent heart damage if any artery completely occludes.

Performing a coronary angioplasty involves the additional difficulty of inserting the balloon catheter into the desired coronary artery. Most balloon catheters are too flexible for direct insertion into a patient's coronary arteries; and accordingly a guide catheter or a guide wire guides the balloon catheter to the proper position in the artery designated for treatment. A cardiologist first inserts the guide catheter or guide wire into the ostium of the artery selected for treatment and then inserts the balloon catheter through the guide catheter to position the balloon across the stenosis. Catheters are generally characterized as being either selective or unselective. Unselective guide catheters ordinarily permit insertion only into the aorta. Various types of selective catheters permit insertion into the left and right main coronary arteries, but are unable to provide reliable means for inserting a balloon into the coronary arteries branching from the main coronary arteries. The catheter sometimes hangs against an arterial wall near an arterial ostium causing trauma, which leads to spasm. Even selective catheters may require a few hours of trial and error for insertion into a coronary artery in some cases, and in some patients, it is impossible to insert a selective catheter into the artery designated to receive the angioplasty treatment without the risk of excessive trauma and spasm in the arteries leading to the stenosis.

Percutaneous balloon valvuloplasty may be an alternative to open heart surgery for certain patients having congenital pulmonary valve stenosis. The catheter and deflated balloon are advanced through the femoral vein and heart to the pulmonary artery and across the stenotic valve. A cardiologist uses a manually operated pumping device to inflate the balloon for four or five seconds at a time.

The balloon contains a radiopaque dye, which permits visual monitoring of the process. Blood flow is occluded through the pulmonary artery during the inflation period, which must, therefore, be as short as possible in order to avoid systemic hypotension and bradycardia. The balloon catheter is withdrawn after the force of the inflated balloon ruptures the valve.

About one of every 1,500 children is born with pulmonary valve stenosis. If the condition is left untreated, the strain of pumping blood through the narrowed pulmonary valve causes excessive pressure in the right ventricle, leading to possible heart failure. Surgical correction of pulmonary valve stenosis requires about ten days of hospitalization, leaves a surgical scar, carries a relatively greater risk of morbidity and mortality and is very expensive. In contrast, balloon valvuloplasty ordinarily requires approximately three days of hospitalization, has a very low morbidity and mortality risk, is performed under local anaesthesia, which is safer than the general anaesthetic required for open-heart surgery and costs about one-third as much as open-heart surgery. Still, however, the necessity of deflating the balloon every four or five seconds is a great inconvenience encountered in the use of prior balloon catheters.

SUMMARY OF THE INVENTION

The present invention overcomes difficulties associated with the use of ordinary coronary dilatation catheters in administering coronary angioplasty and valuloplasty treatments by providing a coronary dilatation catheter which provides blood flow during such treatments. The invention therefore obviates the necessity of removing the catheter from a stenotic artery or valve every five-ten seconds in order to avoid heart damage due to lack of blood flow. Blood flow during an angioplasty treatment provides a lubricant which separates the catheter from the arterial wall, thereby minimizing injury to the patient and assisting the cardiologist in administration of the treatment.

The preferred embodiment of the present invention provides a catheter having a main lumen, or passage, for conducting radiopaque dyes and medication into the heart. This catheter further includes at least one balloon connected thereto for insertion in a blood vessel across the stenosis. The balloon is connected to a minor lumen to receive a pressurized fluid for expanding the balloon, whcih compresses the stenosis radially outward against the walls of the blood vessel. The main lumen terminates in a central outlet at the distal end and preferably has at least one distal side orifice downstream from the balloon. The catheter tube further includes at least one proximal side orifice for admitting blood into the main lumen for passage therethrough past the balloon and the stenosis to the central outlet in the main lumen and the distal side orifice to maintain continuity of blood flow in the blood vessel.

A second embodiment of the invention includes a balloon structure which provides blood flow between the balloon and the blood vessel wall. A single balloon is formed to have a lobed configuration so that blood flow passages exist between the blood vessel wall and the regions between the lobes when the lobed balloon is inflated in a blood vessel. Blood flows through the passages past the inflated balloon. This second embodiment also includes a plurality of balloon segments mounted angularly spaced apart around the circumference of the catheter tube. When the balloon segments are expanded in a blood vessel, blood flows through blood flow passages between the blood vessel wall and adjacent balloons.

A third embodiment of the invention further provides a catheter preformed to provide insertion into coronary arteries which branch away from a main coronary artery. Since the term "selective" is used in the art to denote catheters adapted for insertion into specific main coronary arteries, the term "superselective" is used herein to connote a catheter designed for insertion into remote coronary arteries. The superselective catheter has a pair of distal bends which facilitate insertion thereof into the branch coronary arteries. This embodiment also includes a superselective guide wire for guiding a catheter into remote arteries.

The invention further includes a catheter designed to have a closed loop configuration at the distal end to facilitate catheterization of the right coronary artery, which is generally more difficult to intubate than the left coronary artery.

A fifth embodiment of the invention further includes a system including two preformed guide catheters for inserting a balloon catheter into a branch coronary artery. An outer guide catheter is positioned in the ostium of a main coronary artery, and the inner guide catheter is inserted through the outer guide catheter and maneuvered into position so that the distal end thereof enters the ostium of a branch coronary artery. After the inner guide catheter is positioned in the desired branch coronary artery, a balloon catheter, preferably having distal and proximal side orifices, is inserted through the inner guide catheter into the desired artery and across the stenosis.

Thus the invention provides an alternative to surgery for many patients having stenotic arteries or stenotic pulmonary valves by permitting blood flow during treatment of the stenotic region and by providing means for superselective insertion of a balloon catheter into a desired location in the heart. The invention is useful in catheterization of any blood vessel in which blood flow cannot be interrupted for more than a few seconds without causing damage to the patient.

BRIEF DESCRIPTION OF THE DRAWINGS

FIG. 1 illustrates a ballon catheter having blood flow passages;

FIG. 2 is a partial cross-sectional view illustrating the balloon catheter of FIG. 1 positioned inside a patient's artery with the balloon inflated;

FIG. 2a is a partial cross sectional view taken along line 2a—2a of FIG. 2;

FIGS. 3-7 illustrate superselective catheters;

FIGS. 14A-14C illustrate components of a superselective catheter system;

FIG. 15 illustrates the system of FIGS. 14A-14C being assembled together for insertion into a patient's coronary artery;

FIG. 16 illustrates the catheter of FIG. 14A being inserted into a patient's coronary artery;

FIG. 17 illustrates the catheter of FIG. 14B being inserted through the catheter of FIG. 14A into the patient's coronary artery; and FIG. 18 illustrates the catheter of FIG. 14C being inserted through the catheters of FIGS. 14A and 14B into an artery which branches off from the main coronary artery.

DESCRIPTION OF THE PREFERRED EMBODIMENT DOUBLE-LUMEN BALLOON CATHETER STRUCTURE

Figure 8:
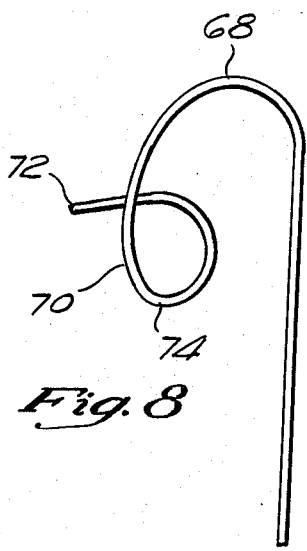
FIG. 8 illustrates a catheter designed for insertion into a patient's right coronary artery.

Referring to FIGS. 1 and 2, a double-lumen balloon catheter 30 includes a distal end 32, a proximal end 34 and a balloon 31 between the distal end 32 and the proximal end 34. The balloon 31 is attached to the catheter 30 by a suitable adhesive or other means well known in the art. The double-lumen balloon catheter 30 includes a main lumen 36 which terminates in a central opening 38 at the distal end 32. The distal end 32 of the balloon catheter 30 may include one or more side orifices 40a, 40b located between the balloon 31 and the central opening 38. The balloon catheter 30 further includes one or more side orifices 42a, 42b, located between the proximal end 34 and the balloon 31. As described below, these side orifices provide fluid communication between the proximal end 34 and the distal end 32.

The catheter 30 is preferably formed of a high strength polyolefin material. The balloon 31 is preferably formed of a thin polyvinyl chloride material which yields a very strong non-compliant balloon capable of withstanding high inflation pressures. The catheter 30 may also be formed of a polyethylene material. Manufacturing techniques for forming the catheter 30 are well-known in the art. The thin walled balloon 31 is designed to inflate to a known diameter at a given pressure to control the forces applied to the stenosis and adjacent arterial walls. The structure of the balloon 31 provides radial compression of the material comprising the stenosis without longitudinal movement of the material, which reduces the danger of shearing and catheter emboli. The inflatable balloon may be adapted in length and maximum external diameter to the diameter of the occlusion and to the anatomy of the affected blood vessel.

The balloon catheter 30 further includes a minor lumen 44, attached thereto as shown in FIGS. 2 and 2a, which supplies a suitable fluid for inflating the balloon 31 from a fluid supply source (not shown) remote from the balloon 31. The balloon 31 is shown inflated inside an artery 46 of a patient in FIG. 2. A pair of annular bands 33 and 35, preferably formed of platinum or gold, at the ends of the balloon 31 are visible on an angiogram to aid in proper positioning of the balloon 31 relative to a lesion.

FUNCTION OF DOUBLE-LUMEN BALLOON CATHETER

As shown in FIG. 2, balloon 31 when inflated completely occludes blood flow past the wall of the artery 46. A significant feature of the present invention is that even when the balloon 31 is fully inflated, blood continues to flow into the side orifices 42a, 42b adjacent the proximal end 34 of the balloon catheter 30, through the main lumen 36 and out of the central opening 38 and the side orifices 40a, 40b at the distal end 32. This flow of blood is illustrated by the arrows which indicate the flow of blood. Thus, the balloon catheter 30 provides means for administering an angioplasty treatment to compress a stenosis adjacent the inflated balloon 31 against the wall of the artery 46 while providing blood flow adequate to prevent heart damage downstream from the inflated balloon 31.

The side orifices 40a, 40b, 42a, 42b offer other significant improvements as well. Thus, they may also provide means for injecting fluids into a blood vessel, the heart, or other organ of the body for therapeutic and diagnostic purposes. These side holes 40a, 40b, 42a, 42b also permit monitoring of blood pressure both proximal and distal to the balloon. Monitoring the distal blood pressure during an angioplasty or valvuloplasty treatment enables medically trained personnel to ascertain the adequacy of blood flow during the treatment to prevent heart damage. The pressure gradient across the stenosis is indicative of the degree to which the stenosis restricts blood flow. After an angioplasty treatment, the pressure gradient across the stenosis should be less than the gradient before the angioplasty. Proximal and distal blood pressure may be measured with the balloon deflated and left across the stenosis. Comparing the proximal and distal pressures permits a determination of whether the treatment has been successful. If the treatment was successful, the catheter 30 may be withdrawn from the patient or moved to another stenotic region. If the treatment failed to restore adequate blood flow, the balloon 31 is normally reinflated for additional treatments until a maximum safe balloon pressure is attained.

PREFORMED CATHETERS

A balloon catheter, such as the catheter 30, is usually too flexible for direct insertion into a coronary artery. Such flexible catheters require the use of a guide catheter or guide wire (not shown) for insertion into a coronary artery such as the artery 46. Guide catheters are available in various preformed shapes, well known in the art, for enabling trained personnel to insert them into selected blood vessels. A balloon catheter preformed for insertion into specific blood vessels simplifies administration of an angioplasty treatment by eliminating the requirement for the guide catheter.

Referring to FIGS. 3 and 4, there is shown a preformed catheter 48. The preformed catheter 48 includes a proximal end 43 preferably having one or more proximal side orifices 50a, 50b, a central orifice 52, and a distal end 45 having one or more distal side orifices 54a, 54b. The catheter 48 may include a balloon 56. When the balloon 56 is expanded to occlude an artery 49, blood flows into the proximal side orifices 50a, 50b and out through the central orifice 52 and the distal side orifices 54a, 54b.

The catheter 48 having a blood flow path formed by the distal orifices 54a, 54b and proximal orifices 50a, 50b, respectively, but not including the balloon 56 is useful in catheterizations for diagnostic and therapeutic purposes, such as injection of medicine and radiopaque dyes. In some patients, particularly those having a left main coronary lesion, insertion of a catheter partially occludes blood flow and causes trauma and spasm. The tip of the catheter may become engaged upon an arterial wall. Blood flow between the proximal and distal portions provides lubrication between the tip of the catheter 48 and the adjacent arterial walls to reduce the risk of trauma and spasm.

FIGS. 5-7 illustrate a configuration which may advantageously be used to form either a superselective guide wire or a second preformed catheter 55. As shown in FIGS. 5-7, the preformed catheter 55 includes distal end 57 which has a first distal bend 58, a second distal bend 62, and a proximal bend 60, which facilitate insertion of the distal end 49 of the catheter 55 into a branch coronary artery 68 shown in FIGS. 16-18. By controlling the longitudinal and angular positions of the distal end 57 of the preformed catheter 55, a cardiologist may first insert the preformed catheter 55 into a patient's aorta and then into a main coronary artery. The distal bend 58 provides means by which a cardiologist can advance the catheter 55 into the ostium of an artery which branches off from the main coronary artery. Therefore, the catheter 55 of FIGS. 5-7, is superselective because it provides means for guiding the distal end 57 into arteries remote from a main coronary artery.

Referring to FIG. 5, a connecting portion 64 connects the proximal bend 60 and the distal bends 58 and 62. FIG. 6 is a plan view of the catheter 55 of FIG. 5, wherein the proximal bend 60 and the second distal bend 62 appear to be straight lines colinear with the connecting portion 64. The distal curved portion 58, as shown in FIG. 6, has an angular deviation from the connecting portion 64 of one to approximately thirty degrees, the exact angle depending upon the particular artery in which the catheter 55 is to be inserted.

When a guide wire is formed to have the proximal bend 60 and the distal bends 58, 62, the guide wire may be used for superselective insertion of a catheter such as the catheter 30. The guide wire is inserted into the heart by conventional methods and then into the coronary arteries using the bends 60, 58 and 62. The catheter 30 is slipped over the guide wire into the selected artery.

The proximal bend 60, the distal bend 58 and the distal bend 62 may all lie in different planes. The first distal bend 58 and the second distal bend 62 are shown in an examplary orientation. The angle between the first distal bend 58 and the second distal bend 62 may be opposite to that shown in FIGS. 5–7.

FIG. 8 shows still another configuration for a superselective catheter 66. The catheter 66 of FIG. 8 has a proximal curved portion 68 having a bend of approximately 180° and a distal curved portion 70 having a 360° bend, formed near a distal end 72 which causes the distal end 72 of the catheter 66 to form a closed loop as seen in FIG. 8. The catheter 66 may also include a balloon, such as the balloon 31 described above with reference to FIGS. 1, 2 and 2a. The catheter 66 of FIG. 8 may be inserted into the aorta using a guide catheter (not shown). The catheter 66 is then advanced out of the guide catheter so that a point 74 approximately central to the distal cruved portion 70 contacts the aortic wall. Further advancement of the catheter 66 causes the point 74 to react against the aortic wall to force the distal end 72 of the catheter 66 into the desired coronary artery.

BALLOON STRUCTURES

Figure 10A:
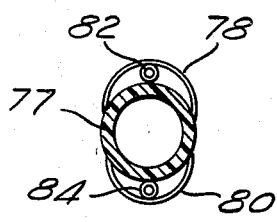
FIG. 10a is a cross sectional view taken along line 10—10 of FIG. 9.
Figure 10B:
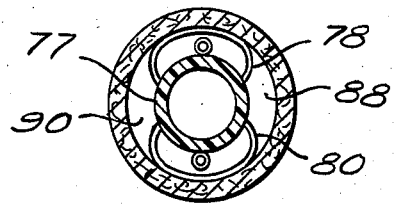
FIG. 10b is a cross sectional view showing the catheter of FIG. 9 inflated in a blood vessel.
Figure 9:
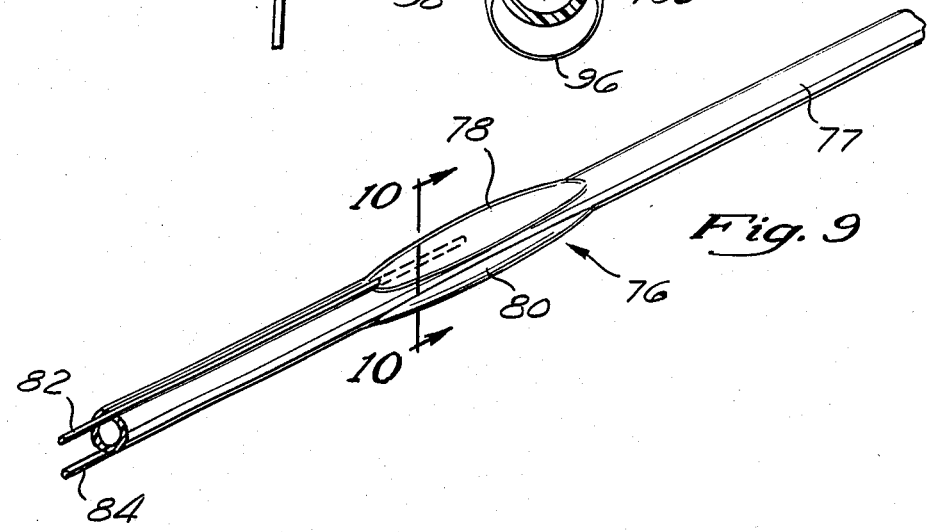
FIG. 9 is a perspective view of a catheter containing two angularly spaced apart balloons.

Referring to the embodiment shown in FIGS. 9 and 10a, a balloon catheter 76 includes a pair of balloons 78, 80 connected to the outer surface of a tube 77. As shown in the cross sectional views of FIGS. 10a and 10b, each of the balloons 78, 80 covers approximately one-half of the circumference of the tube 77. In an embodiment having separate balloons 78, 80 which have edges attached lengthwise along the tube 77, each of the balloons has a corresponding minor lumen 82, 84. The minor lumens 82 and 84 provide fluid for expanding the balloons 78 and 80, respectfully. As shown in FIG. 10b, when the balloons 78, 80 are expanded, the central portions thereof exert radially opposing forces on opposite portions of the arterial wall. However, blood flow is provided past the inflated balloons 78, 80 through a pair of cavities 88 and 90 adjacent the regions of the balloons 78, 80 connected to the tube 77.

Figure 10C:
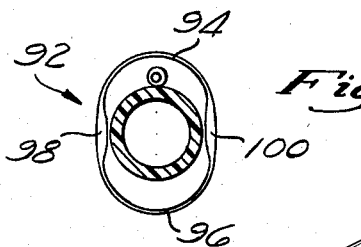
FIG. 10c is a cross sectional view of a second embodiment of the catheter of FIG. 1.

Referring to FIG. 10c, instead of having separate balloons attached to the tube 77, there may be a single balloon 92 having a pair of lobes 94 and 96 with portions 98 and 100 between the lobes 94 and 96 being formed to have thicker walls than the lobes 94 and 96, which expand to contact the arterial wall. Inflation of the lobed balloon 92 causes the lobes 94 and 96 to expand radially outward to compress a stenosis while the thicker portions 98 and 100 remain in close proximity to the exterior surface of the tube 77 to provide blood flow past the balloon 92.

Figure 11:
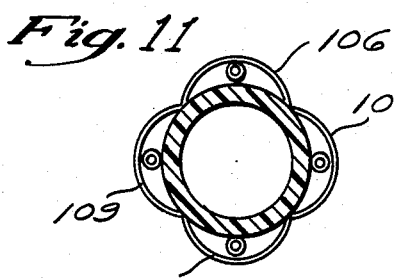
FIG. 11 is a cross sectional view of a balloon catheter including four angularly spaced-apart balloons.

As shown in FIG. 11, a balloon catheter 76 has four separate balloons 106–109 or lobes with the structure of each balloon or lobe 106–109 being similar to that of the balloons or lobes 78 and 80 of FIGS. 10a–10c.

The catheters of FIGS. 9–12 are suitable for use in angioplasty regardless of whether the arterial wall lesions are uniform or nonuniform. If a segmented or lobed balloon catheter fails to achieve desired results when inflated in a particular angular orientation in a blood vessel, it is a simple procedure for trained personnel to deflate the balloon, or balloons, rotate the catheter and reinflate the balloons to effect additional widening of the blood flow path.

Figure 12:
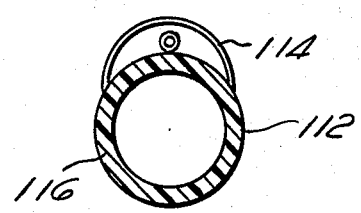
FIG. 12 is a cross-sectional view of a balloon catheter illustrating a balloon covering a portion of the circumference of the catheter tube.

Referring to FIG. 12, a double-lumen balloon catheter 112 has a balloon 114 which extends over only a portion of the circumference of the tube 116. The balloon catheter 112 of FIG. 12 is particularly useful in treating a patient having a stenosis on only one side of an artery, which is not uncommon. If the stenosis is localized on only one side of the artery, prior balloon catheters exert unnecessary radially outward forces on a localized portion of normal arterial wall tissue, which results in unnecessary trauma and edema and possibly spasm in the arterial wall. After proper positioning, the balloon 114 applies a localized radially outward force to a stenosis while distributing the forces applied to normal arterial wall tissue over an area larger than the area of the stenosis, thereby minimizing trauma and edema to normal tissue.

Figure 13:
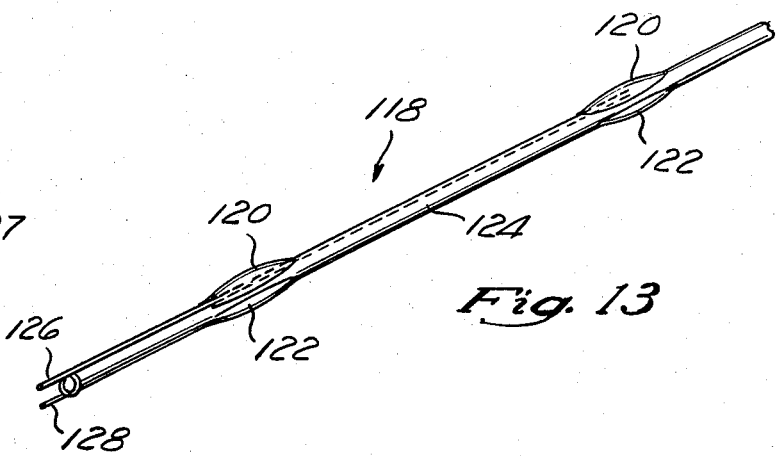
FIG. 13 is a perspective view illustrating a balloon catheter having two balloons displaced apart along the length of the catheter tube.

Referring to FIG. 13, a balloon catheter 118 may include a plurality of balloons 120, 122 attached thereto with the balloons 120 and 122 being spaced apart along the length of a tube 124. The balloons 120 and 122 may circumferentially enclose tube 124 or the balloons 120 and 122 may be made similar to the balloons of FIGS. 9–12. The balloons 120, 122 may be serially connected to a minor lumen 126 or, alternatively, there may be a second minor lumen 128 so that each of the balloons 120, 122 has a corresponding minor lumen to permit selective inflation of one of the balloons 120, 122 without inflating the other. The catheter of FIG. 13 having spaced apart balloons 120, 122 is useful in treating more than one lesion at a time in an artery having multiple lesions. The catheter 118 may be furnished with any desired number of balloons with any convenient spacing between adjacent balloons 120 and 122. The catheter 118 provides means for permitting treatment of more than one stenosis at a time while requiring minimal or no manipulation, resulting in less trauma to the blood vessel than if an ordinary balloon catheter were manipulated into position in each stenosis for administering angioplasty treatment at different times to the various stenotic regions. The catheter 118 of FIG. 13 includes side orifices (not shown in FIG. 13) similar to those of FIGS. 1 and 2 for permitting blood flow during angioplasty treatment.

SUPERSELECTIVE CATHETER SYSTEM

FIGS. 14a–14c illustrate separate components of a superselective coronary angioplasty dilatation catheter system 130. FIG. 14a illustrates a preformed outer guide catheter 132 having a preformed distal end 133, which may be inserted in the ostium 134 of a coronary artery 136 as shown in FIG. 16. The outer guide catheter 132 is inserted into an incision in the patient's left femoral artery and may require the use of a guide wire or other guide catheter (not shown) to straighten out the preformed distal portion 133 until the distal end 133 is adjacent the ostium 134 of the desired coronary artery 136. After the outer guide catheter 132 is positioned in the desired ostium 134, the guide wire or other guide catheter is removed and an inner guide catheter 138, shown in FIG. 14b, is inserted through the outer guide catheter 132 so that a distal end 140 of the inner guide catheter 138 is in a position proximate the branch coronary artery 63 as shown in FIG. 17. A cardiologist or other trained person rotates the outer and inner guide catheters 132 and 138, respectively, and controls the penetration of the distal ends 133 and 14 in the artery 136 to position the distal end of the inner guide catheter in the ostium of the branch artery 63 as shown in FIG. 18. After the inner guide catheter 138 is positioned within the ostium of the branch artery 63, a balloon catheter 142 such as the balloon catheters illustrated and described with reference to FIGS. 1–13, is inserted through the inner guide catheter 138 into the branch artery for administration of an angioplasty treatment.

Some cardiologists prefer to use a guide wire 144 for inserting a balloon catheter even when the balloon catheter is inserted into a guide catheter such as the inner guide catheter 138. The guide wire 144 is pushed out of the inner guide catheter and a balloon catheter 142, which may be straight or preformed, is pushed over the guide wire 144.

What is claimed is:

1. A method of administering an angioplasty treatment to a patient to produce acceptable blood flow in a stenotic region of a coronary artery having restricted blood flow, comprising:
    inserting a tube having an outer surface enclosing a main lumen terminating in a main axial orifice into said coronary artery, said tube having a proximal portion and a distal portion;
    inflating a balloon attached to the outer surface of said tube between said proximal portion and said distal portion to compress said stenotic region;
    channeling blood flow through the wall of said proximal portion of said main lumen immediately adjacent said balloon to fluidly connect locations within said coronary artery surrounding said proximal and distal portions of said tube while said balloon is inflated within said coronary artery to conduct blood downstream from the portion of said coronary artery occluded by the inflated balloon.

2. A method of administering an angioplasty treatment to a patient to produce acceptable blood flow in a stenotic region of a coronary artery having restricted blood flow, comprising:
    inserting a tube having an outer surface enclosing a main lumen terminating in a main axial orifice into said coronary artery, said tube having a proximal portion and a distal portion;
    inflating a plurality of balloons attached at a single location along the length of, but angularly spaced apart on the outer surface of said tube between said proximal portion and said distal portion to compress said stenotic region;
    channeling blood flow through said coronary artery between the proximal and distal portions of said tube while said balloon is inflated within said coronary artery to conduct blood downstream from the portion of said coronary artery occluded by the inflated balloon by allowing blood to flow between the walls of said plural balloons and the arterial walls.

3. A catheter system for superselective administration of an angioplasty treatment to a patient's blood vessel to restore acceptable blood flow in a stenotic region of the blood vessel having restricted blood flow, comprising:
    an outer guide catheter, said outer guide catheter being preformed into a bent configuration for insertion into a predetermined blood vessel;
    an inner guide catheter formed to fit inside said outer guide catheter, said inner guide catheter being preformed into a bent configuration to extend out of said outer guide catheter into the ostium of a branch blood vessel which branches from said predetermined blood vessel; and
    a balloon catheter formed for insertion through said inner guide catheter into the branch blood vessel across the stenotic region therein whereby said balloon catheter may be inserted with said inner and outer catheters in place in the patient.

4. A method of superselective administration of an angioplasty treatment to a stenotic region of a patient's blood vessel having restricted blood flow, comprising the steps of:
    inserting an outer guide catheter preformed with a bend into a first blood vessel;
    inserting an inner guide catheter preformed with a bend through said outer guide catheter into a second blood vessel which branches from the first blood vessel;
    inserting a balloon catheter through said inner guide catheter into the second blood vessel across the stenotic region without removing said inner or outer guide catheter from said patient; and
    supplying a pressurized fluid to the balloon to expand the balloon radially outward against the stenotic region to compress the stenotic region against the blood vessel.

5. The method of claim 4 further including the step of channeling blood flow through said balloon catheter past the stenotic region while said balloon is inflated.

6. The method of claim 5 further including the step of forming the balloon to allow blood to flow between portions of the balloon and the blood vessel when the balloon is inflated.

7. The catheter system of claim 3 further including a guide wire for insertion into said inner guide catheter for guiding said balloon catheter after said balloon catheter extends from said inner guide catheter.

8. The method of claim 5 further including the step of inserting a guide wire inside said inner guide catheter.

* * * * *

REEXAMINATION CERTIFICATE (2302nd)
United States Patent [19]
Sahota

[11] B1 4,581,017
[45] Certificate Issued May 17, 1994

[54] CATHETER SYSTEMS

[75] Inventor: Harvinder Sahota, Seal Beach, Calif.

[73] Assignee: C.R. Bard, Inc., Murray Hill, N.J.

Reexamination Request:
No. 90/003,076, Jun. 1, 1993

Reexamination Certificate for:
Patent No.: 4,581,017
Issued: Mar. 7, 1983
Appl. No.: 473,063
Filed: Apr. 8, 1986

[51] Int. Cl.$^5$ .............................. A61M 29/00
[52] U.S. Cl. ........................... 604/101; 604/102
[58] Field of Search .................................. 604/102

[56] References Cited

U.S. PATENT DOCUMENTS 3,834,394  9/1974  Hunter et al.
4,224,929  9/1980  Furihata
4,423,725  1/1984  Baran et al.

OTHER PUBLICATIONS

King et al., Coronary Arteriography and Angioplasty, 1985, chapter 15, pp. 399-416, McGraw-Hill.
Meier et al., Experimental Percutaneous Arterial Perfusion of Occluded Coronary Arteries with a Roller Pump.
C. R. Bard v. Advanced Cardiovascular Systems, Inc. No. 89-1719 (CAFC).

*Primary Examiner*—John Yasko

[57] ABSTRACT

Catheter systems provide blood flow paths past a stenotic region of a blood vessel receiving treatment to restore acceptable blood flow. A catheter includes distal and proximal side orifices into a main lumen to provide a blood flow path through the catheter across the stenosis. A segmented or lobed balloon forms blood flow passages between the catheter and blood vessel wall to provide blood flow past the stenosis while the balloon is inflated. Superselective catheter systems provide means for inserting a catheter into coronary arteries remote from the aorta.

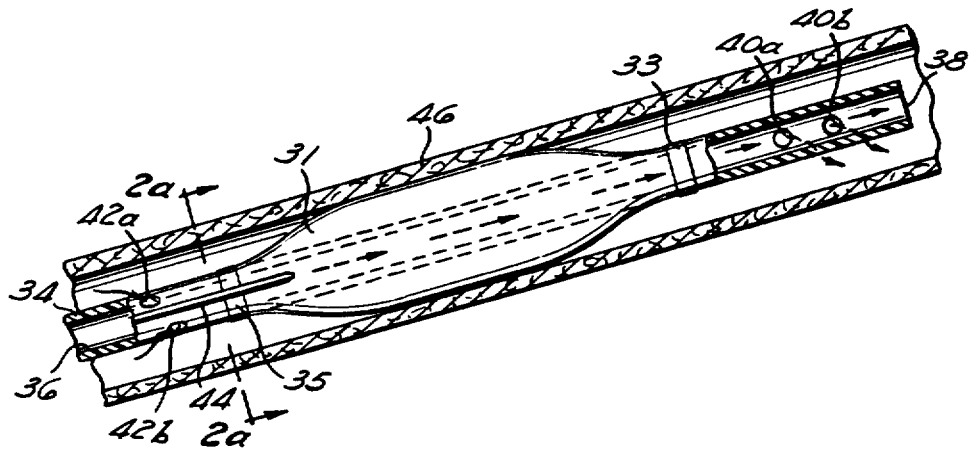

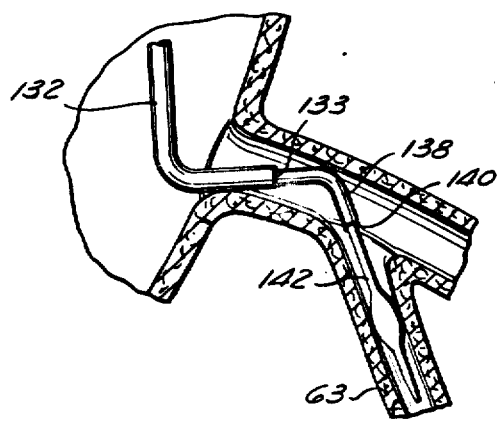

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-8 is confirmed.

* * * * *